United States Patent
Lütjens et al.

(10) Patent No.: US 7,125,165 B2
(45) Date of Patent: Oct. 24, 2006

(54) C-ARM X-RAY APPARATUS HAVING MEANS OF CALIBRATION

(75) Inventors: Jörn Lütjens, Bremen (DE); Volker Rasche, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/538,444

(22) PCT Filed: Dec. 1, 2003

(86) PCT No.: PCT/IB03/05618

§ 371 (c)(1),
(2), (4) Date: Jun. 10, 2005

(87) PCT Pub. No.: WO2004/052205

PCT Pub. Date: Jun. 24, 2004

(65) Prior Publication Data

US 2006/0109957 A1    May 25, 2006

(30) Foreign Application Priority Data

Dec. 11, 2002    (EP)    .................... 02102719

(51) Int. Cl.
*A61B 6/08*    (2006.01)
*H05G 1/02*    (2006.01)

(52) U.S. Cl. ................. 378/205; 378/196; 378/197

(58) Field of Classification Search ............. 378/65, 378/196, 197, 205, 206, 207
See application file for complete search history.

(56) References Cited

U.S. PATENT DOCUMENTS

| 5,622,187 | A | * | 4/1997 | Carol | ................... 128/897 |
| 6,050,724 | A |   | 4/2000 | Schmitz et al. | |
| 6,120,180 | A | * | 9/2000 | Graumann | ............ 378/206 |
| 6,206,566 | B1 | * | 3/2001 | Schuetz | ............ 378/205 |
| 6,213,638 | B1 | * | 4/2001 | Rattner | ............ 378/198 |
| 6,575,624 | B1 | * | 6/2003 | Noegel et al. | ............ 378/198 |
| 2001/0027263 | A1 |   | 10/2001 | Zylka et al. | |

FOREIGN PATENT DOCUMENTS

EP    0 910 990 A1    4/1999

* cited by examiner

*Primary Examiner*—Edward J. Glick
*Assistant Examiner*—Irakli Kiknadze

(57) ABSTRACT

The invention relates to an X-ray apparatus having a C-arm assembly (1) on which an X-ray source (4) and an X-ray detector (5) are arranged opposite one another, the C-arm assembly (1) being arranged to be rotatable about a propeller axis (9) and an axis of rotation (11). To enable calibration to take place even on-line during the acquisition of projected data, respective marker arrangements (14, 15) are mounted on the X-ray source (4) and the X-ray detector (5), and a camera arrangement (12) for detecting the marker arrangements (14, 15) is arranged on the C-arm assembly (1) to allow the positions of the X-ray source (4) and the X-ray detector (5) to be determined. With this arrangement, the problem of the blocking of lines of sight between the marker arrangements (14, 15) and the camera arrangement (12) is reduced or completely avoided.

14 Claims, 2 Drawing Sheets

C-ARM X-RAY APPARATUS HAVING MEANS OF CALIBRATION

The invention relates to an X-ray apparatus having a C-arm assembly on which an X-ray source and an X-ray detector are arranged opposite one another, the C-arm assembly being arranged to be rotatable about a propeller axis and an axis of rotation that extend perpendicularly to one another, and having respective marker arrangements mounted on the X-ray source and the X-ray detector.

Modern-day pieces of vascular C-arm X-ray apparatus are capable of acquiring projected data from different directions of projection, from which data 3D images of a subject being examined can be reconstructed. In this case, the C-arm assembly can generally be rotated about an axis of rotation that is always perpendicular to the plane in which the C-arm assembly lies, and about a propeller axis that is perpendicular to the axis of rotation and passes through the point at which the C-arm assembly is mounted. The intention is that these functions should now also be made available to mobile pieces of C-arm X-ray apparatus that are smaller, less rugged and not tied to a fixed location.

Known pieces of fixed and especially mobile C-arm X-ray apparatus do, however, have mechanical instabilities that relate in particular to the adjustment of the C-arm assembly longitudinally of its circumference, as a result of which the actual adjusting movement of the C-arm deviates from the ideal adjusting movement. This being the case, the determination of the angle of projection is often affected by errors, as a result of which the quality of the 3D images reconstructed from the 2D projections suffers. Pieces of mobile C-arm X-ray apparatus in particular, which were not originally designed for 3D imaging, are not strong enough mechanically to reproduce the desired projection geometry with sufficient accuracy. Therefore, either their geometry has to be measured while the projected data is being acquired or else the X-ray apparatus has to be pre-calibrated for all projection geometries.

When the systems are being calibrated, there are two main problems that may occur. A first problem is that the system may not repeat exactly. What this means is that hen asked to do the same thing, the system does not behave in the same way. Not even a complete calibration can do anything about this, because the encoder cannot be mapped cleanly enough onto the system. A second problem is that the system may be operated at uncalibrated points, particularly because calibration cannot be carried out at an infinitely large number of points. Both problems may occur. Pre-calibration for all possible orientations solves only the second problem and not the first.

The majority of pieces of C-arm X-ray apparatus make use of a calibration procedure. In this, the positions and orientations of the X-ray source and X-ray detector are measured repeatedly in three-dimensional space, for all the positions to be calibrated. The values measured are stored in a reference table and can later be used when projected data is being acquired. The measurement of position can be performed by analyzing X-ray projections of a calibration phantom or by means of an external measuring system.

Calibration while projected data is being acquired calls for the use of a measuring device that is capable of determining the parameters of interest, namely position of focus, detector position and attitude, for any desired angle of acquisition, and without affecting the acquisition of the projected data itself to any excessive degree. However, with optical locating techniques, there is the problem that in many positions the patient blocks the direct line of sight between the means of measurement. To overcome this problem, a camera is mounted at the side of the X-ray detector in one known piece of X-ray apparatus. However, even this method only works for a limited range of positions of the C-arm assembly and it also requires the position of the X-ray detector relative to the stationary parts of the X-ray apparatus to be measured. The absolute position of the detector cannot be determined in this way.

An X-ray unit in which the X-ray detector and the X-ray source each have an ultrasonic emitter arranged on them and there are a plurality of ultrasonic receivers arranged on the mounting device for the C-arm assembly is known from EP 0 910 990 A1. In this case too, however, it is necessary for the line of sight between the emitters and receivers not to be blocked by the patient, something that is not possible in all positions. Another problem that exists in this case is that of temperature-sensitivity, because the speed of sound varies greatly with temperature. Non-optical methods of measurement, which are based on magnetic fields or electromagnetic waves for example, are often subject to interference and considerably more expensive than optical methods.

It is therefore an object of the present invention to provide an X-ray apparatus with which calibration to current conditions is possible during the acquisition of the projected data and in which the problem that has been described of the blocking of the direct line of sight between the position measuring elements is avoided.

This object is achieved in accordance with the invention by an X-ray unit as defined in claim 1, in which a camera arrangement for detecting the marker arrangements mounted on the X-ray source and the X-ray detector is provided for determining the positions of the X-ray source and X-ray detector, the camera arrangement being arranged on the C-arm assembly.

The invention is based on the idea of arranging the camera arrangement in such a way that the direct line of sight between the camera arrangement and the marker arrangements cannot be blocked by the patient regardless of the projection geometry at the time. The C-arm assembly itself has proved to be an ideal mounting point for the camera arrangement in this case. The field of vision of the camera arrangement is then so large that the marker arrangements can always be seen in any projection geometry. In a preferred embodiment, there are two camera arrangements provided, one being trained on the marker arrangement mounted on the X-ray detector and the other on the marker arrangement mounted on the X-ray source.

Preferred embodiments of the X-ray apparatus according to the invention are detailed in the dependent claims. In one such embodiment, provision is made for the camera arrangement to be arranged on a part of the C-arm assembly whose position does not change when the C-arm is rotated about the axis of rotation. This may, for example, be done by arranging the camera arrangement on that axis of revolution of the C-arm assembly that is situated along the propeller axis, i.e. approximately at the point where the C-arm is supported. So that, when the C-arm moves about the axis of rotation, the camera arrangement then does not move with the arm, there may for example be arranged in the C-arm of the C-arm assembly, for almost the entire length of the arm, a central slot or slider in which or on which the camera arrangement travels along, or rather remains fixed, when the C-arm rotates, and the C-arm, as its rotates, slides past the camera arrangement. The view of vision of the at least one camera of the camera arrangement is then arranged to be of an appropriate size to enable the two marker arrangements to be seen in all the rotated positions.

To also enable the marker arrangements always to be seen when the C-arm assembly rotates about the propeller axis, the field of vision of the camera arrangement is arranged to be of a suitable size in the direction of the axis of rotation. As an alternative, the camera arrangement may however also be so arranged, as is provided for in another embodiment, that, when the C-arm assembly rotates about the propeller axis, the camera arrangement moves with the assembly, so that in rotation of this kind the angular position of the camera arrangement is always the same as the angular position of the X-ray source and X-ray detector. Angle encoders may also be provided in this case to encode the angle.

In an alternative embodiment, however, the camera arrangement is arranged on a part of the C-arm assembly whose position changes if the C-arm rotates about the axis of rotation. Hence, when this is the case, the position of the camera arrangement is always the same relative to the positions of the X-ray detector and the X-ray source, and the angular view of vision of the camera arrangement can thus be relatively small. With this embodiment there is, however, a reliable guarantee that the marker arrangements can be seen whatever position the camera arrangement is in, and the probability of the lines of sight being blocked by the subject of the examination is also very small, in which case any such blockages can be, completely ruled out if the camera arrangement is suitably arranged.

In this embodiment, it is preferable for the camera arrangement to be arranged on the displaceable C-arm carrying the X-ray source and the X-ray detector, in particular in a central position between the X-ray source and X-ray detector. Hence, the camera arrangement, just like the X-ray detector and the X-ray source, then shares in rotational movements about the axis of rotation and about the propeller axis but is not subject to the mechanical instabilities to which the X-ray source and X-ray detector are exposed, or is hardly subject to them.

Provision is also made in a special embodiment for a marker arrangement also to be mounted on the camera arrangement, which marker arrangement is detected by a further, fixed camera arrangement to enable the positions in space of the camera arrangements arranged on the C-arm assembly to be determined. The fixed camera arrangement may, for example, be arranged on a non-moving part of the X-ray apparatus, on a stand or in a fixed position in the room, on the ceiling, for example.

The camera arrangement and the marker arrangements preferably operate by optical methods. In this way, the marker arrangements may, for example, be small light emitters, such as light-emitting diodes for example, which are detected by a camera operating in the optical range. A marker arrangement is so designed in this case that, from its detection, the position in three dimensions of the element on which it is arranged can be determined with the greatest possible accuracy. Each marker arrangement may, for example, have three individual markers mounted at different points. Alternatively however, the marker arrangement may also be a particular recognition pattern that enables position to be determined.

However, other methods besides the optical method may also be used, such as, for example, methods that operate in the infrared range or the ultrasonic range, i.e. infrared or ultrasonic emitters and receivers. For these too, a direct line of sight has to be ensured between the emitting and receiving elements.

These and other aspects of the invention are apparent from and will be elucidated with reference to the embodiments described hereinafter.

Figure 1:
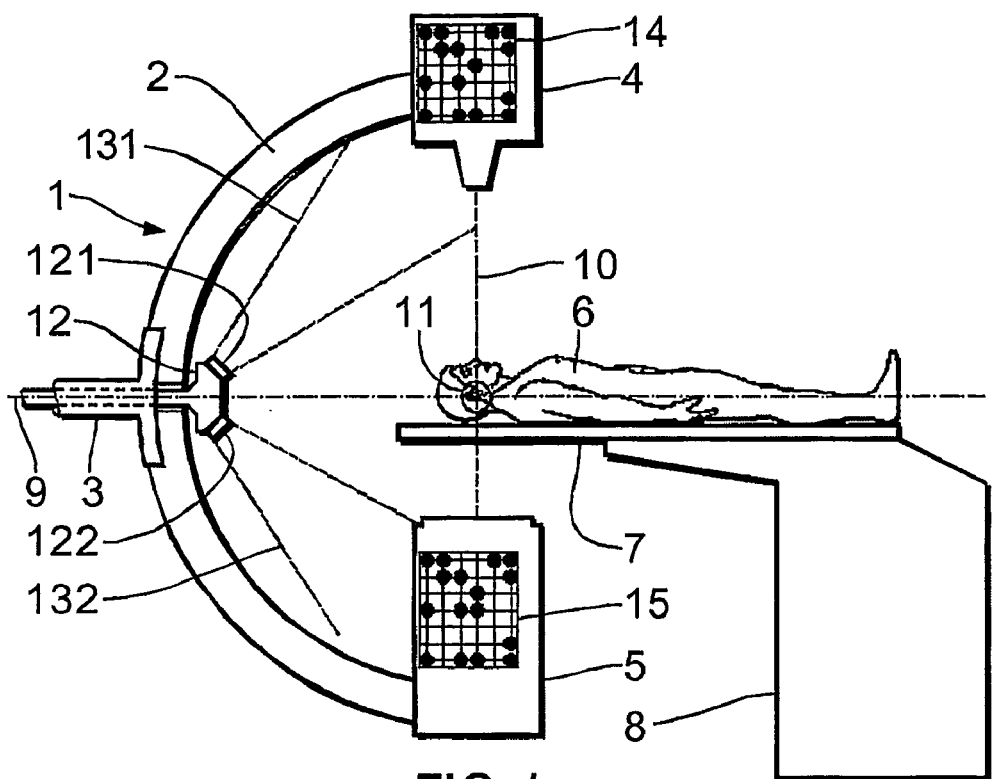
FIG. 1 shows a first embodiment of X-ray apparatus according to the invention in a first projection geometry.

FIG. 1 shows a first embodiment of C-arm X-ray apparatus according to the invention. The apparatus has a C-arm assembly 1 having a C-arm 2 and a mounting arrangement 3. Arranged opposite one another at the ends of the C-arm 2 are an X-ray source 4 and an X-ray detector 5. To allow X-ray images to be generated, a subject for examination, in the present case a patient 6, lies on a patient table 7 that is mounted on a pedestal 8. By means of the mounting arrangement 3, the C-arm 2 can be rotated about a propeller axis 9 that extends in the horizontal direction in the drawing. The C-arm 2 itself can be rotated relative to the mounting arrangement 3 about an axis of rotation 11 that extends perpendicularly to the plane of the drawing and to the connecting line 10 between the X-ray source 4 and the X-ray detector 5. In this way, it is possible for a plurality of projection geometries to be set to enable a series of X-ray projection images to be acquired, from which a 3D data set relating to the subject of examination 6 can be reconstructed.

In accordance with the invention, there is also a camera arrangement 12 provided that in the present case comprises two individual cameras 121 and 122 that in turn have respective fields of vision 131 and 132. The camera arrangement 12 is arranged on the propeller axis 9 but is not solidly connected to the C-arm. A slot that extends for substantially the entire length of the C-arm 2, and that thus extends in the plane of the drawing and cannot be seen in FIG. 1, allows the C-arm to be rotated about the axis of rotation 11 without the camera arrangement 12 being moved with the arm.

Mounted on both the X-ray source 4 and the X-ray detector 5 are also respective marker arrangements 14 and 15 which each have a pattern of optical markers. These make it possible for the position of the X-ray source 4 and the X-ray detector 5 in which the cameras 121, 122 sense the positions of the individual markers to be determined exactly. It is assumed in this case that the marker arrangements occupy fixed and known positions relative to the X-ray detector 5 and the X-ray source 4 and that the position of the camera arrangement too is known.

Figure 2:
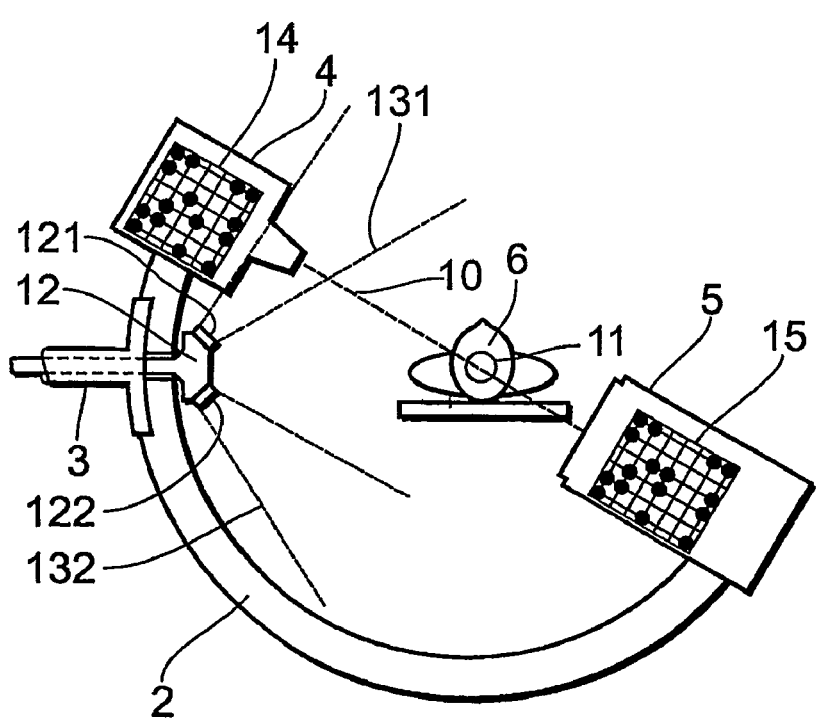
FIG. 2 shows the first embodiment in a second projection geometry.

As can be seen from FIG. 2, the patient 6 no longer blocks the fields of vision 131, 132 of the cameras 121, 122, except possibly at extreme angles of rotation about the axis of rotation 11 and/or when the patient 6 is in extreme positions, such as if, for example, he approaches very close to the camera arrangement 12. Because in the embodiment shown the camera arrangement 12 is so arranged that it is not moved during the acquisition of projected data, its fixed relationship to the isocenter, i.e. the point of intersection between the propeller axis 9, the connecting line 10 and the axis of rotation 11, can be used to obtain a simple relationship with the laboratory coordinate system.

A disadvantage that this configuration has can also be seen in FIG. 2. In this embodiment, the angular range of rotation is limited not only as a result of the mechanical arrangements but also by the limited angular field of vision of the cameras 121, 122. In an extreme projection geometry of the kind shown in FIG. 2, where the distance between the camera 121 and the marker arrangement 14 is too small, the marker arrangement 14 is no longer situated within the field of vision 131 of the camera arrangement 121. Where the field of vision 132 of the camera 122 is of the form shown, the marker arrangement 15 too is situated outside this field of vision 132. As a result, it is no longer possible for the positions of the X-ray source 4 and the X-ray detector 5 to be determined in extreme projections geometries of this kind. However, since a circular or semi-circular trajectory is often followed in 3D X-ray imaging, for which only rotation about the propeller axis is required, this problem does not arise in a majority of applications.

In the embodiment shown, the camera arrangement may be so arranged that it is fully fixed and, when rotation takes place either about the axis of rotation 11 or about the propeller axis 9, it does not share in this movement. When the C-arm assembly 1 rotates about the propeller axis 9, it is however also conceivable for the camera arrangement 12 to co-rotate in the same way, to enable it always to detect the marker arrangements 14 and 15 from the same viewing angle.

Figure 3:
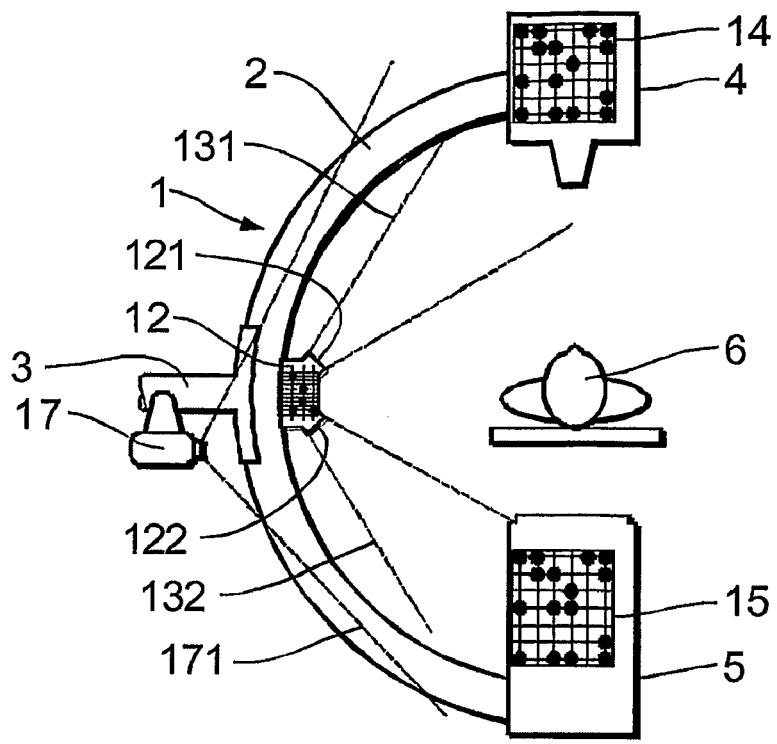
FIG. 3 shows a second embodiment of X-ray apparatus according to the invention in a first projection geometry.

FIG. 3 shows a further embodiment of X-ray apparatus according to the invention. In this embodiment, the camera arrangement 12 is not arranged to be fixed on the propeller axis 9 or on the mounting arrangement 3 but is arranged in a fixed position on the C-arm 2 itself. What this means is that, if the C-arm 2 is rotated about the axis of rotation 11, the camera arrangement 12 moves with the arm and its position relative to the X-ray tube 4 and the X-ray detector 5 thus always remains the same. To a large degree, this almost completely prevents the patient 6 from being able to block the lines of sight between the camera arrangement 12 and the marker arrangements 14, 15, or the marker arrangements from being able to escape from the directed fields of vision 131 and 132. As a result, the fields of vision 131 and 132 may also be made smaller than in the first embodiment.

Figure 4:
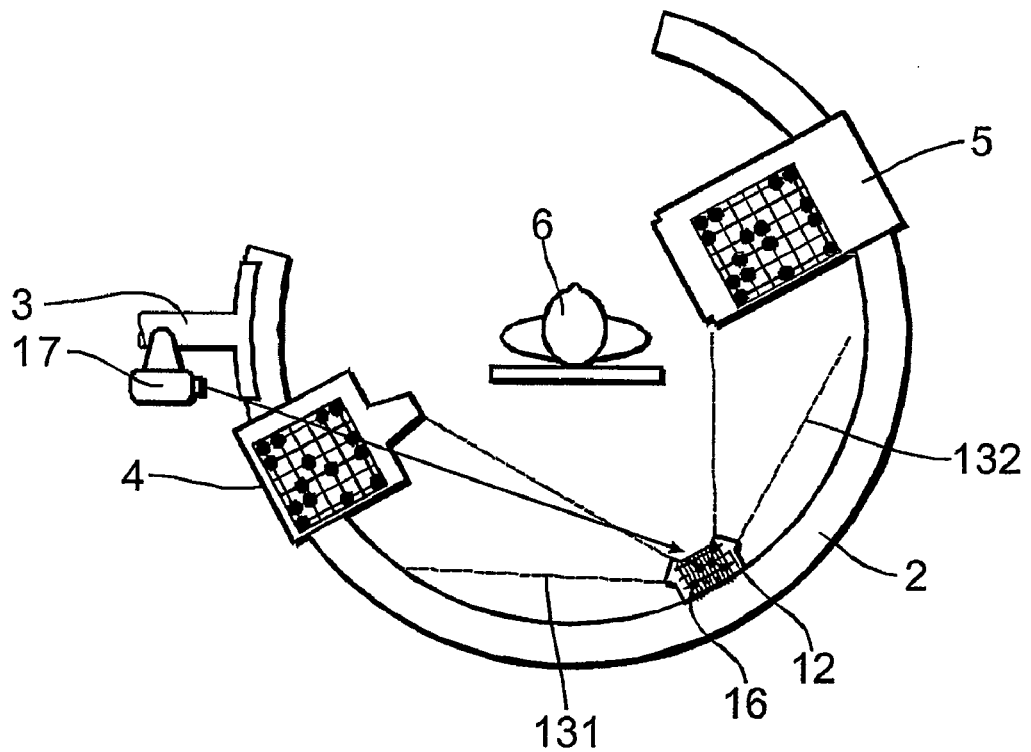
FIG. 4 shows the second embodiment in a second projection geometry.

However, in this embodiment there is no longer a fixed relationship between the camera arrangement 12 and the isocenter, because the camera arrangement 12 does in fact move with the C-arm 2. However, to create a correlation with the laboratory coordinate system, a further camera arrangement 17 having a field of vision 171 is therefore provided, which camera arrangement 17 is arranged in a fixed position, on the mounting arrangement 3 for example, and detects a marker arrangement 16 mounted on the camera arrangement 12. In this way, the position of the camera arrangement 12 can be determined at all times, as a result of which it is, in the final analysis, also possible for the position in space of the X-ray source 4 and the X-ray detector 5 to be determined. As can be seen from FIG. 4, in which the embodiment shown in FIG. 3 is seen in a different projection geometry, the angular field of vision of the camera arrangement 17 must be sufficiently large to enable the marker arrangement 16 mounted on the camera arrangement 12 to be detected in all positions.

In the second embodiment, the C-arm 2 can make a complete rotation about the propeller axis 9. What is also possible is a range of rotation of more than 180° for rotation about the axis of rotation 11, in which case it is only the angular range of vision of the camera arrangement 17 and the mechanism of the C-arm that restrict the range of rotation.

It should be mentioned that the camera arrangement 17 does not necessarily have to be mounted on the mounting arrangement 3. It may in fact be arranged in a fixed position somewhere in the room, on a stand for example or on the ceiling. It must, however, be ensured that the marker arrangement 16 can always be detected.

Even while projected data is being acquired and in any projection geometry, the X-ray apparatus according to the invention make it possible for the position of the X-ray detector and the X-ray source to be determined in relation to a reference coordinate system, to enable calibration to current conditions, taking place on-line, to be performed on this basis. This calibration is thus not dependent on long-term changes in the structural strength of the C-arm, on the corresponding local conditions caused by the force of gravity or on slight deviations from the horizontal shown by the floor of the room.

The invention claimed is:

1. An X-ray apparatus having
   an X-ray source,
   an X-ray detector,
   a C-arm assembly on which the X-ray source and the X-ray detector are arranged at least substantially opposite one another, the C-arm assembly being arranged so as to be rotatable about a propeller axis and an axis of rotation, which axes extend perpendicularly to one another,
   marker arrangements mounted on the X-ray source and the X-ray detector respectively, and
   a camera arrangement for detecting the marker arrangements to enable the positions of the X-ray source and the X-ray detector to be determined, the camera arrangement being arranged on the propellar axis so as to remain stationary when the C-arm assembly rotates about the axis of rotation.

2. The X-ray apparatus as claimed in claim 1, wherein the camera arrangement is arranged on a part of the C-arm assembly whose position does not change when the C-arm assembly is rotated about the axis of rotation.

3. The X-ray apparatus as claimed in claim 2, wherein the camera arrangement is arranged on the axis of revolution of the C-arm assembly that extends along the propeller axis.

4. The X-ray apparatus as claimed in claim 2, wherein the camera arrangement is so arranged that, when the C-arm assembly rotates about the propeller axis, it too performs the rotation.

5. The X-ray apparatus as claimed in claim 1, wherein the camera arrangement is arranged on a part of the C-arm assembly whose position changes if the C-arm assembly is rotated about the axis of rotation.

6. The X-ray apparatus as claimed in claim 5, wherein the camera arrangement is arranged on the C-arm, which C-arm can be traversed about the axis of rotation when the C-arm assembly is rotated and carries the X-ray source and the X-ray detector, the camera arrangement being in particular arranged centrally on the C-arm between the X-ray source and the X-ray detector.

7. The X-ray apparatus as claimed in claim 5, wherein a further marker arrangement is mounted on the camera arrangement and in that the X-ray apparatus also has a fixed camera arrangement for detecting this marker arrangement, which latter is mounted on the camera arrangement arranged on the C-arm assembly to allow the position of this camera arrangement to be determined.

8. The X-ray apparatus as claimed in claim 1, wherein the camera arrangement mounted on the C-arm assembly has two cameras, the first camera detecting the marker arrangement mounted on the X-ray source and the second camera detecting the marker arrangement mounted on the X-ray detector.

9. The X-ray apparatus as claimed in claim 1, wherein a computing unit is provided for the correction by calculation of the image data obtained, by reference to the data obtained relating to the positions of the X-ray source and the X-ray detector.

10. An X-ray apparatus comprising:
   an X-ray source having a first marker arrangement;
   an X-ray detector having a second marker arrangement;
   a C-arm assembly on which the X-ray source and the X-ray detector are mounted; and
   a camera arrangement connected to a portion of the C-arm assembly as to remain stationary when the C-arm is rotated about an axis, and moves when the C-arm assembly is rotated about another axis.

11. The X-ray apparatus of claim 10, wherein the portion of the C-arm assembly to which the camera arrangement is connected is fixed.

12. The X-ray apparatus of claim 10, wherein the portion of the C-arm assembly to which the camera arrangement is connected is moveable.

13. The X-ray apparatus of claim 12 further comprising a second camera arrangement connected to either a fixed or movable portion of the C-arm assembly.

14. The X-ray apparatus of claim 10 further comprising a means for determining the position of the camera arrangement.

* * * * *